United States Patent
Haasmaa et al.

(10) Patent No.: US 6,656,984 B1
(45) Date of Patent: Dec. 2, 2003

(54) HYDROPHOBIC POLYMER DISPERSION AND PROCESS FOR THE PREPARATION THEREOF

(75) Inventors: Kristiina Haasmaa, Espoo (FI); Timo Petteri Paronen, Kuopio (FI); Arto Olavi Urtti, Kuopio (FI); Soili Peltonen, Rajamäki (FI); Maija Elina Heikkilä, Espoo (FI); Jani Vuorenpää, Rajamäki (FI)

(73) Assignee: Oy Polymer Corex Kuopio Ltd., Kuopio (FI)

( * ) Notice: Subject to any disclaimer, the term of this patent is extended or adjusted under 35 U.S.C. 154(b) by 0 days.

(21) Appl. No.: 09/202,981
(22) PCT Filed: Jun. 25, 1997
(86) PCT No.: PCT/FI97/00410
§ 371 (c)(1), (2), (4) Date: Feb. 24, 1999
(87) PCT Pub. No.: WO97/49762
PCT Pub. Date: Dec. 31, 1997

(30) Foreign Application Priority Data

Jun. 25, 1996 (FI) .................................................. 962627

(51) Int. Cl.$^7$ ................................. C08J 5/10; C08L 3/00
(52) U.S. Cl. ..................... 524/51; 524/47; 524/503; 524/313; 524/297; 524/50; 524/52
(58) Field of Search .......................... 523/177; 524/47, 524/50, 56, 57, 58, 503, 37, 38, 39, 41, 46, 312, 313, 270, 297, 51, 52

(56) References Cited

U.S. PATENT DOCUMENTS

| | | | |
|---|---|---|---|
| 3,746,558 A | 7/1973 | Berkhout et al. | ........... 106/213 |
| 4,061,611 A | 12/1977 | Glowaky et al. | ..... 260/17.4 ST |
| 5,498,648 A | * 3/1996 | de Clercq et al. | ............ 524/47 |
| 6,020,422 A | * 2/2000 | Connors et al. | ............ 524/716 |

FOREIGN PATENT DOCUMENTS

SE       374116        2/1997

* cited by examiner

Primary Examiner—James J. Seidleck
Assistant Examiner—U. K. Rajguru
(74) Attorney, Agent, or Firm—Birch, Stewart, Kolasch & Birch, LLP

(57) ABSTRACT

The invention relates to a hydrophobic polymer dispersion and a solvent-free process for the preparation thereof. According to the invention, the dispersion contains starch ester together with dispersion admixtures known as such. According to the process, the polymer is first mixed with a plasticizer in order to obtain a plasticized polymer blend. The plasticized polymer blend is then mixed with dispersion admixtures and water at an elevated temperature so as to form a dispersion. The plasticizing of the polymer and the dispersion of the mixture in water can be performed in an extruder. The obtained dispersion is homogenized in order to improve its stability. The dispersion obtained by the invention can be used to coat paper or board, as a primer or a component in paint or labeling adhesives, and it is also suitable for the production of cast films and as a binder in materials based on cellulose fibers, as well as for coating medicinal preparations.

35 Claims, 1 Drawing Sheet

HYDROPHOBIC POLYMER DISPERSION AND PROCESS FOR THE PREPARATION THEREOF

Figure 1:
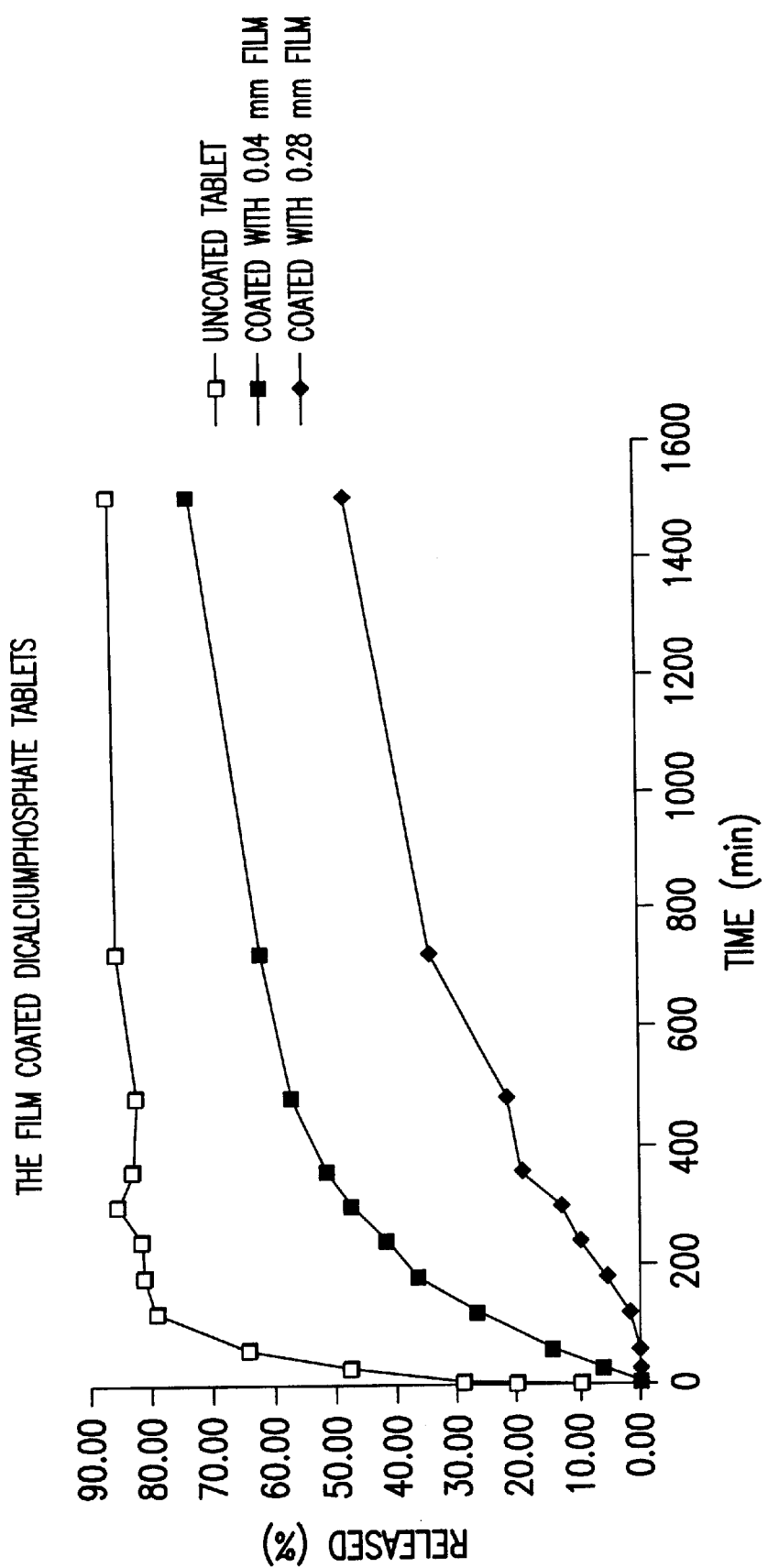

This application is the national phase under 35 U.S.C. §371 of prior PCT International Application No. PCT/FI97/00410 which has an International filing date of Jun. 25, 1997 which designated the United States of America.

The present invention relates to a hydrophobic polymer dispersion according to the preamble of claim 1.

Such a dispersion contains modified starch dispersed in a liquid phase together with admixtures which are used in dispersions and known as such.

The invention also relates to a process according to the preamble of claim 16 for the formation of a hydrophobic polymer dispersion.

The emphasis on an environmentally friendly attitude and green values is opening up new markets for products based on renewable natural resources. Such trends are emerging in the fields of, among others, the packing industry, the sanitary product industry and the adhesive industry, where recyclability, reuse, compostability, biodegradability and lack of environmental stress are demands of today. The trend of replacing products based on petrochemistry by processed biopolymer products is also accentuated. Starch and its derivatives constitute a particularly interesting starting material for the production of biodegradable polymer products.

Polymer dispersions are used, e.g., to coat paper and board so as to improve their water resistance. In addition to fillers, dispersions used within the paper industry today also contain various synthetic latexes which are quite poorly decomposed in a biological environment.

Solutions are previously known in which modified starch components are used for the preparation of paper coating dispersions. Thus, a coating composition is known from WO Published Application No. 93/11300, based on a polymer dispersion containing a starch derivative having a polymer grafted thereto containing styrene and butadiene monomers. Therefore. this solution makes no use of such biodegradable components which are compatible with the demands on recyclability set on the products.

The present invention aims at achieving a hydrophobic dispersion most or preferably essentially all of whose components are biodegradable. The invention particularly aims at producing a dispersion whose polymer component mainly comprises a biodegradable polymer, advantageously starch or a derivative thereof. Furthermore, the invention seeks to provide a process for the production of hydrophobic dispersions.

The invention is based on the surprising observation that many biodegradable polymers can advantageously be dispersed in water by first plasticizing them and by dispersing the plasticized melt in water using dispersion admixtures. Thereby no solvents are required for producing the dispersion. Thus, according to the present process, as the polymer, a biodegradable polymer is used, first mixed with a plasticizer in order to obtain a plasticized blend, the blend is mixed with admixtures and water in optional order so as to obtain a dispersion, whereby the mixing is carried out at an elevated temperature, and if desired, the dispersion is homogenized.

In more detail, the dispersion according to the invention is mainly characterized by what is stated in the characterizing part of claim 1.

The process according to the invention. then, is characterized by what is stated in the characterizing part of claim 16.

The invention provides considerable benefits. Thus, the base materials of the starch dispersion according to the invention are mainly based on renewable natural resources and are biodegradable/compostable. The starch component may be derived from any native starch: it need not be, e.g. a starch rich in amylose. No solvents requiring removal by evaporation are needed for the formation of the dispersion instead, the dispersion may be carried out by means of a melt processing apparatus, whereby the consumption of plasticizer is simultaneously considerably reduced. The films formed from the dispersion have a high water repellence and can be used to improve the water resistance of paper or board by at least 40 to 50%.

The new polymer dispersions may be used for coating paper or board, as a primer or as a component in labelling adhesives or paint. They are also suited for the production of hydrophobic cast films and for use as binders in materials based on cellulose fibres.

A particularly interesting embodiment comprises use of polymer dispersions for coating, for instance, medicinal preparations in tablet form.

The coating of medicinal preparations in tablet form is as such a very commnon process within the pharmaceutical industry. The purpose of the coating is either to cover the disagreeable taste or smell of the drug, to protect the drug against external factors during storage or dosage, to facilitate the packaging, identification or dosage of the tablets, or to control the release of active substance from the tablet. The most demanding ground for coating pharmaceutical tablets is the aim of obtaining controlled, usually retarded release of the active substances. The purpose is to achieve a desired rate of absorption by the body of the active substance over a longer time span. The purpose may, however, even lie in achieving the release and absorption of an active substance in a certain part of the digestive tract, this being the optimal part for the absorption of the medicinal preparation in question.

As a pharmaceutical process, the coating of tablets with a polymer film is carried out by spraying a solution or dispersion containing the coating polymer onto the tablets and by then evaporating the solvent or medium by means of pressurized air. Traditionally, polymers dissolved in organic solvents have been used for coating tablets containing medicinal preparations. Typical examples comprise ethyl cellulose and hydroxypropyl methyl cellulose. During the past few years, this technology has been developed especially for water-based coatings. In such a case the coating polymer is either soluble in water or dispersible in water. Polymers which are dispersible in water offer a wider range of possible uses from the point of view of controlling the release of active substances than do those soluble in water. Ethyl cellulose, among others, is available in the form of aqueous dispersions.

The use of aqueous dispersions is aimed at because organic solvents are environmentally less friendly and cause more problems for those dealing with them at work. The change is, however, not entirely free from complications, because the elaboration of dispersion processes is most demanding and not nearly all of the currently used polymers can be used to yield a dispersion. Furthermore, industrial processes for the preparation of drugs often have such dissimilar details that the same coating methods and equipment cannot be used in all cases. In addition, the properties of polymer films made from aqueous dispersions are often essentially different from those of films made from organic solutions.

The present invention can be used to obtain polymer dispersions particularly suited for coating pharmaceutical preparations. The dispersions are especially well suited for coating solid pharmaceutical preparations, such as pharmaceutical preparations with prolonged effect. As examples of pharmaceutical preparations subjected to coating, tablets, capsules and pellets may be cited, as well as particle-shaped drug carrier and allocator systems, such as nanoparticles, nanocapsules, microparticles, and colloidal dispersions. The release rate of a pharmaceutical substance may be controlled by regulating the thickness of the polymer film formed. By modifying the dispersion formulation, an optimal release profile for the medicinal preparation is easily obtained.

The invention is examined in more detail in the following in the light of a detailed description and a number of working examples.

The annexed FIGURE is a graphic pesentation of the release of active substance from dicalcium phosphate tablets coated with dispersions according to the present invention.

Hydrophobic starch dispersions can be produced by means of the process described herein. containing as the starch component a starch ester, starch ether, mixed ester/ether of starch or grafted starch made from native starch, hydrolyzed starch, oxidized starch, crosslinked starch, or gelatinized starch. Hydrophobic polymer dispersions can also be prepared form other biodegradable polymers such as polycaprolactone, lactic acid polymers, polylactide and/or polyhydroxyburyrate/-valerate. The last mentioned polymers can naturally be used in mixtures with starch polymers. Most advantageously, hydrophobic starch ester containing polymer dispersions are obtained.

In the composition according to the invention, starch or a derivative thereof, in the following also called starch component. may be based on any native starch having an amylose content of 0 to 100% and an amylopectin content of 100 to 0%. Thus, the starch component may be derived from barley, potato, wheat, oat, pea, corn, tapioca, sago, rice, or a similar ruber-bearing or grain plant. It may also be based on starches prepared from said native starches by oxidizing, hydrolyzing, crosslinking, cationizing, grafting, etherifying or esterifying.

It has proved advantageous to use a starch-based component derived from an ester formed by starch and one or several aliphatic $C_{2-24}$ carboxyl acids. The carboxyl acid component of such an ester may then be derived from a lower alkane acid, such as acetic acid, propionic acid or butyric acid, or a mixture thereof. The carboxyl acid component may, however, even be derived from a saturated or an unsaturated native fatty acid. Examples of these include palmitic acid, stearic acid, oleic acid, linoleic acid, and mixtures thereof. The ester may also also consist of both long- and short-chain carboxyl acid components. As an example, a mixed ester of acetate and stearate may be cited.

The preparation of fatty acid esters of starch is carried out. for example, in the manner described in the publications Wolff, I. A., Olds, D. W. and Hilbert, G. E., The acylation of Corn Starch, Amylose and Amylopectin. J. Amer. Chem. Soc. 73 (1952) 346–349, or Gros, A. T. and Feuge. R. O., Properties of Fatty Acid Esters of Amylose, J. Amer. Oil Chemists' Soc 39 (1962) 19–24.

Starch acetates can be prepared by allowing the starch to react with an acetanhydride in the precence of a catalyst. As catalyst, a 50% sodium hydroxide is used, for example. Even the other known processes for the preparation of acetates are suited for the preparation of starch acetate. By varying the amount of acetic acid anhydride, the amount of the base used as catalyst as well as the reaction duration, starch acetates with different degrees of substitution may be prepared.

The starch component is advantageously an esterified starch, preferably a starch acetate with a degree of substitution between 0.5 and 3, advantageously 1.5 and 3 and most suitably 2 and 3. It is particularly preferred to use, e.g., enzymatically hydrolyzed barley starch for the preparation of starch esters.

As stated above, the starch component is given a plastic form by admixing it with a softening agent or plasticizer known as such. For this purpose, the dispersion composition according to the invention is made to contain preferably 0.01–95% by weight, advantageously about 1–50% by weight of plasticizer. Any known plasticizers can be used, such as triacetin, diacetin, monoacetin, triethyl citrate, tributyl citrate, acetyl triethyl citrate, acetyl tributyl citrate, dimethyl succinate, diethyl succinate, ethyl lactate, methyl lactate, fatty acid esters of glycerol, castor oil, olive oil. rapeseed oil, tall oil, dibutyl phthalate, diethyl phthalate, and mixtures thereof.

The starch dispersion further contains a dispersion admixture which allows for the dispersion of the plasticized polymer melt in sufficiently fine particles in water so as to form a stable dispersion. As an example of dispersion admixtures, polyvinyl alcohol (PVA) may be cited, in particular PVA whose weight-average molar mass is about 10,000 to 115,000. Other dispersion admixtures (protective colloids) include cationic starch and hydroxyalkyl starch, whereby these can be used separately or together with PVA. The dispersions may further contain alkyl-ketene dimer (AKD) wax and beeswax as additives or admixtures.

As an example of advantageous polymer dispersion compositions, a composition may be cited containing 5 to 25 parts by weight of a starch ester, 5 to 50 parts by weight of a plasticizer, 1 to 150 parts by weight of water, and 1 to 20 parts by weight of a dispersion admixture.

Typically, water is present in an amount which is 2 to 10 times, preferably about 4 to 6 times, and plasticizer in an amount which is about 0.1 to 2 times, and admixture in an amount which is about 0.1 to 1.5 times the amount of the biodegradable polymer. Thus, as regards, for example, the preparation of a hydrophobic starch ester dispersion, it can be cited that about 1.0 to 5 kg of starch ester, 0.5 to 6 kg of plasticizer, and about 0.1 to 1.5 kg of admixture may be dispersed in 10 kg of water.

Depending on the intended use, such a polymer dispersion may even be made to include 0.01 to 30% by weight, preferably about 5 to 30% by weight of a cellulose ester, such as cellulose acetate. cellulose propionate or cellulose butyrate, or mixed esters theraof.

The present dispersion compositions are prepared by dispersing a plasticized polymer melt in water with the aid of admixtures. In order to achieve plasticizing, the biodegradable polymer is admixed with the plasticizer suitably at an elevated temperature so as to form a melt. On a small scale, the plasticizing may be carried out in, e.g., a flask equipped with a reflux condenser and efficient mixing. The temperature varies according to the plasticizer used but is typically about 50 to 250° C., preferably about 100 to 200° C. On a larger scale, the plasticizing is advantageously carried out in a melt processing apparatus, such as an extruder.

The plasticized melt is dispersed in liquid phase, usually water, using admixtures. Water is a particularly preferred dispersion medium according to the invention, but the invention may also be applied such that various solvents are used.

The admixture and water may be added in optional order, Thus, the admixture may first be added to the plasticized polymer melt, whereafter the water or admixture may be dissolved in water and added along with the water. In both cases, a gradual addition of water is preferred. Most suitably, the addition of water and admixture is performed with a velocity allowing the mass to remain homogeneous without any separation of phases. According to an advantageous embodiment. this is achieved by bringing water in drops or otherwise in small quantities into the hot plasticized biopolymer, e.g., a starch derivative or starch, by means of a pump. During the addition, the condensing of the evaporating water is seen to, whereafter it is brought back into the mixture. When starch-based dispersions are prepared, it is particularly beneficial to first add a small amount of water dropwise into the molten mass, and the addition is interrupted for some time, typically 5 to 30 minutes, so as to make sure that the mass is well mixed and homogeneous. Next, the adding of water dropwise can be continued until all of the water has been added. In the case of other biodegradable polymers, water can be added without interruptions.

According to one advantageous embodiment, the dispersion is prepared by admixing 5 to 25 parts by weight of a starch ester with 5 to 50 parts by weight of a plasticizer so as to obtain a plasticized starch ester mixture, keeping the liquid phase at a temperature of about 100 to 180° C. during mixing, and adding 1 to 150 parts by weight of water and 1 to 20 parts by weight of a dispersion admixture into the plasticized starch ester mixture, whereby the liquid phase is kept at a temperature of about 50 to 100° C. while adding the water.

According to another particularly advantageous embodiment the dispersion is prepared by intermixing in a polymer melt processing machine at 100 to 250° C.

5 to 25 parts by weight of a starch ester, 5 to 50 parts by weight of a plasticizer, 1 to 20 parts by weight of an admixture for forming a plasticized starch ester blend, and by admixing the plasticized starch ester blend into 1 to 150 parts by weight of water at a temperature of about 50 to 100° C. in order to form a hydrophobic dispersion.

The dispersion can, however, also be carried out by mixing the admixture with water and by merely intermixing the starch ester and plasticizer in the melt processing machine.

After dispersing, the dispersion is, if desired, homogenized in a manner known per se in order to stabilize it. Homogenization can, for instance, be achieved by means of a pressure homogenizer. As will emerge from Example 2, homogenization can be used to reduce particle size by 50 to 100%, thus improving the stability of the dispersion. Dispersions according to the invention will remain stable for several weeks, even months.

The invention can be used to obtain dispersions of biodegradable polymers, preferably starch derivatives, in particular starch esters, with 90% of the polymer particles smaller than 10 $\mu$m. By homogenizing, dispersions are obtained with average particle sizes below 2 $\mu$m or even below 1 $\mu$m. According to the intended use, dispersions can father be prepared with a multimodal, in practice usually bimodal, particle size distribution.

The following non-limiting examples will illustrate the invention. The starch acetate substitution degrees given in the examples have been determined according to Wurzburg (Wurzburg, O. B. Acetvlation, in *Methods in Carbohydrate Chemistry*, Vol. IV, ed. R. L. Whistler, Academic Press, New York and London. 1964, p. 288). The molar masses have been determined by GPC analysis in the research laboratory of Alko Group Ltd. The apparatus was a HP-1090 comprising two columns in a cascade (Waters, Ultra Hydrogel 2000), the solvent was 50 nM NaOH, the temperature 40° C., dextran standards, detectors: RI and viscosity detectors. The molar mass has been determnined for the starch used as raw material.

EXAMPLE 1

Enzymatically Hydrolyzed Starch

An enzymatically hydrolyzed starch suited for the preparation of starch esters is obtained by adding thermo-$\alpha$-amylase into a water suspension of starch whereafter the suspension is passed through a jet cooker and steam is added. The enzyme is allowed to act until the starch is sufficiently degraded. The process is monitored by measuring the viscosity of the suspension. When the desired viscosity has been reached, the enzyme is inactivated and the starch is dried.

EXAMPLE 2

Starch Acetate Dispersion 50.0 g of a starch acetate from enzymatically hydrolyzed barley starch, prepared according to the method disclosed in WO Pat. No. 95/33450 and exhibiting a DS of 2.8, and 87.5 g of triacetin (Unichema: Priacetin) are melted in a flask equipped with a reflux condenser under heating using an electric bath and intensive stirring with a blade mixer until a homogeneous and translucent mixture is obtained. At this point, the temperature of the mixture is approximately 160° C. Polyvinyl alcohol is added to the melt in an amount of 16.3 g (Hoechst, molar mass 20 000 and degree of hydrolysis 74%) and stirred for 10 min. whereafter 12 ml of water at a temperature of about 90° C. is slowly added. The stirring is continued for another 15 min whilst slowly adding 213 g of hot (about 90° C.) water without disrupting the stirring. The temperature is kept at approximately 95° C. After adding the water, the stirring is continued for another 15 min whereafter the mixture is allowed to cool to room temperature in a water bath. The viscosity of the homogeneous dispersion obtained measured with a Bohlin viscosimeter, the shear rate being. e.g. 2.92E+2 l/s, is 2.05E-1 Pas and the average particle size 2.7 $\mu$m, and 90% of the particles are below 7.2 $\mu$m measured with a particle size analyzer based on laser diffraction.

Where further reduction of the particle size is desired, the solution can be subjected to homogenization using a pressure homogenizer whereby, at a pressure of 1000 bar, the average particle size is reduced to 2.0 $\mu$m:iin and 90% of the particles are below 4.8%. If the treatment is repeated, an average particle size of about 1.5 $\mu$m is attained, whereby 90% of the particles are below 3.6 $\mu$m.

The dispersion will maintain its stability at room temperature for several weeks. The viscosity of the solution can be regulated by varying the amount of water added.

EXAMPLE 3

Starch Acetate Dispersion Containing AKD Wax 50.0 g of a starch acetate made from enzymatically hydrolyzed barley starch and having a DS of 2.8,77.5 g of triacetin (Unichema: Priacetin) and 10.0 g of alkyl-ketene dimer wax (Raisio Chemicals: Raisares A) are melted in a flask equipped with a reflux condenser under heating using an electric bath and intensive stirring with a blade mixer until a homogeneous and translucent mixture is obtained. 12 ml of hot (90° C.) water is slowly added, whereafter polyvinyl alcohol is added in an amount of 16.3 g (Hoechst. molar mass 20 000 and degree of hydrolysis 74%) and the mixture is strred for 10 min. Next, hot water is added in an amount of 208 g under intensive (400 rpm) stirring. The mixture is kept at a temperature of 90–95° C. Cooling to about 30° C. in a water bath under continuous intensive stirring. The viscosity of the homogeneous dispersion obtained measured with a Bohlin viscosimeter, the shear rate being, e.g. 2.92E+2 l/s, is 6.29E−1 Pas.

EXAMPLE 4

Starch Acetate Dispersion With Hydroxypropyl Starch as Admixture

In accordance with Example 2. 50.0 g of a starch acetate is plasticized having a DS of 2.8. with 87.5 g of triacetin. Hydroxypropyl starch (Primalco, COHPOL LLIOO) having a MS of 0.4 is dissolved in an amount of 16.3 g into 220 g of water. A hot hydroxypropyl starch solution is added in an amount of 12 ml into the homogeneous melt which is then stirred for 15 min, whereafter the rest of the hydroxypropyl starch solution is slowly added under continuous intensive stirring. simultaneously keeping the temperature of the mixture at about 90° C. The result is a homogeneous stable dispersion wherein the hydroxypropyl search acts as a protective colloid, and no phase separation is observed.

EXAMPLE 5

Starch Acetate Dispersion With Cationized Starch as Admixture 50.0 g of starch acetate from enzymatically hydrolyzed barley starch, with a DS of 2.8, and 87.5 g of triacetin (Unichema: Priacetin) are melted in accordance with Example 2. 4.0 g of cationized starch (Raisio Chemicals: Raisamyl 150) is dissolved into 220 g of warm water. Hot starch solution is added in an amount of 12 ml into the homogeneous melt and stirred for 15 min whereafter the rest of the starch solution is gradually added under intensive stirring whilst maintaining the temperature of the mixture at about 90° C. A homogeneous milk-like dispersion is obtained with a viscosity which, measured with a Bohlin viscosineter, the shear rate being, e.g., 2.92E+2 l/s, is 6.06E−1 Pas.

When the dispersion obtained is used to rod coat board which has a Cobb60 value, measured using the Cobb test according to Tappi T 441 om-90, of 24.5 g/m², said value indicating the water adsorption capacirv of the board, a Cobb60 value of 17.2 g/m² is obtained for coated board when the film thickness is 24.2 g/m², that is, the coating achieves a board water resistance which has been improved by 30%.

EXAMPLE 6

Starch Acetate Dispersion With Dimethyl Succinate and AKD Wax as Admixtures 50.0 g of a starch acetate from enzymatically hydrolyzed barley starch, with a DS of 2.8, and 87.5 g of dimethyl succinate (Fluka) are melted in a flask equipped with a reflux condenser under heating using an electric bath and intensive stirring with a blade mixer at a temperature of 115° C. until a homogeneous and translucent mixture is obtained. Alkyl-ketene dimer wax (Raisio Chemicals: Raisares A) is admixed into the melt, the temperature of the mixture is maintained at 115° C., and the mixrare is stirred for 5 min. 16.3 g of polyvinyl alcohol (Hoechst, molar mass 20 000 and degree of hydrolysis 74%) is added and the mixture is stirred for 10 min. Hot water is gradually added in an amount of 12 mil under continuous stirring, the stirring is continued for 15 min and 208 g of hot water is added. A homogeneous dispersion is obtained with a viscosity which, measured with a Bohin viscosimeter, the shear rate being, e.g., 2.92E+2 l/s, is 7.57P−1 Pas. When the dispersion obtained is used to rod coat board which has a Cobb60 value of 23.5 g/m², a Cobb60 value of 8.8 g/m² is obtained for coated board when the film thickness is 18.0 g/m², that is, the coating achieves a board water resistance which has been improved by 62%.

EXAMPLE 7

Dispersion of Known Biopolymers

Commersially available biopolymers, polyhydroksybutyrate/-valerate, and, correspondingly, poly-ε-caprolactone, were dispersed using the process of Example 2.

The compositions of the dispersions are shown in the table below.

TABLE 1

Compositions of the dispersions of biopolymers

| Material | 1 | 2 | 3 |
|---|---|---|---|
| PHB/PHV a) | | 50.0 g | |
| Poly-ε-caprolactone b) | 50.0 g | | |
| PLLA c) | | | 50.0 g |
| Polyvinyl alcohol d) | 16.0 g | 16.0 g | 16.0 g |
| water | 200 g | 200 g | 200 g | a) Zeneca, Biopol D 310G
b) Union Carbide. Tone 767
c) Neste Chemicals
d) Hoechst. molar mass 20000, degree of hydrolysis 74%

When using polyhydroxybutyrate/-valerate, a granular dispersion was obtained which after 7 d was clearly fractionated.

Poly-ε-caprolactone achieved a dispersion which, visually estimated, was homogeneous and stable and which after several weeks of storage was divided into different phases.

PLLA achieved a homogeneous dispersion which remained stable for less than 3 d.

EXAMPLE 8

Starch Palmitate Dispersions

An acid hydrolyzed starch was prepared as described in WO Patent Application No. 95/33450. The starch palmitates were prepared in accordance with the method of FI Patent Application No. 954742.

Starch palmitate and dibutyl phthalate are melted in a flask at 60 to 95° C. in accordance with the melting point of the palmitate. Water or a buffer solution is added into the molten mass at 50 to 60° C. Polyvinyl alcohol has been dissolved in the water or the buffer solution. The addition of water/polyvinyl alcohol is carried out in steps by first adding about 10% of the total amount and then stirring for 15 min. Next, the rest of the water is gradually added and stirred for 20 min whilst keeping the temperature of the mixture at 60 to 95° C. The mixture is then allowed to cool down to room temperature in about 30 min.

The compositions of the dispersions are shown in weight percentages in the table below.

TABLE 2

Starch palmitate dispersions

| Material | 1 | 2 | 3 | 4 | 5 | 6 |
| --- | --- | --- | --- | --- | --- | --- |
| Starch palmitate | DS 2.8 Base starch native barley 17.5 | DS 0.7 Base starch native barley | DS 2.7 Base starch acid hydrolyzed a) 19.3 | DS 0.7 Base starch acid hydrolyzed b) 18.2 | DS 2.8 Base starch native barley 15.4 | DS 2.7 Base starch acid hydrolyzed a) 19.3 |
| Dibutyl phthalate | 17.5 | | 19.3 | 18.3 | 15.4 | 14.5 |
| Polyvinyl alcohol c) | 3.9 | | 3.4 | 4.2 | 3.5 | 3.4 |
| Surface-active agent Span 20 | | | | | | 4.8 |
| Water | 61.1 | | 58.0 | 59.1 | | 58.0 |
| Buffer solution pH 7 | | | | | 65.6 | | a) Duration of hydrolysis 3 h.
b) Duration of hydrolysis 0.5 h
c) Polyvinyl alcohol (BDH. Molar mass 115000, degree of hydrolysis 87%)

The dispersions were kept at room temperature for several weeks. No phase separation occurred, i.e. the dispersions remained stable.

EXAMPLE 9

Water Permeability of Films Cast From the Dispersions in Diffusion Chamber Tests Films were produced from the starch palmitate dispersions 2 and 4 of Example 8 onto a Teflon-coated glass surface using a film applicator apparatus. The films were dried at room temperature and detached from the glass plate.

The water permeability of a film having an average thickness of 0.1 mm was tested by diffusion chamber tests where the film is placed between two chambers and the penetration of tritium through the film is measured in a 40 mM phosphate buffer at pH 7. The diffused tritium is measured as a function of time by means of a liquid scintillation counter.

During 1 hour, an amount of 2% penetrated the film made from dispersion 2. In the case of Tritium and dispersion 4, about 6% penetrated the film. After three hours, the corresponding values were 10% and 18%.

A corresponding dispersion was prepared from an acetate made from acid hydrolyzed starch and having a DS of 2.5. In weight percentages, the dispersion composition was 16.1% acetate, 24.1% dibutyl phthalate, 3.6% polyvinyl alcohol and 56.2% water. The preparation was carried out as described in Example 7. A film was made from this dispersion, as described for palmitate dispersion above, and subjected to analogous diffusion tests. The penetrated amounts of tritium were 17%/ 0.5 h, 20%/1 h ja 23%/3 h.

Even though the penetration results are only of an indicative nature due to pores in the films caused by the evaporation of water, the pores being visible in SEM pictures (the number and size of the pores being similar in all films), the results will allow of the conclusion that the penetration is slower through a film cast from the dispersion of a palmitate made from native starch than through a corresponding palmitate made from hydrolyzed starch. Penetration is clearly accelerated with shorter ester chains, even if the degree of substitution is higher.

EXAMPLE 10

Moisture Permeability of a Film Manufactured From a Starch Acetate Dispersion

A starch acetate dispersion was prepared according to the process of Example 2. The composition of the dispersion, in weight percentages, was 13% of a starch acetate from enzymatically hydrolyzed starch (DS 2.8), 23% of triacetin, 4.3% of polyvinyl alcohol (molar mass 115,000, degree of hydrolysis 87%), and 59.4% of water. The films were cast as described in Example 9. The test measured the moisture permeability of the films at different moisture contents with parallel determinations.

Calcium chloride used as drying agent was metered into an injection bottle. A film cast from the dispersion was placed at the bottle mouth and the bortle wvas carefully sealed such that a film surface of similar size remained on each bottle for moisture permeability measurement. The bottles were placed in exsiccators with different relative humidities and the weight increase of the drying agent was monitored as a function of time, this indicating the amount of moisture penetrating the film. The results are shown in the table below.

TABLE 3

Permeability of films made from the dispersion

| Time days | Relative humidity 33% | Relative humidity 60% | Relative humidity 80% |
| --- | --- | --- | --- |
| 3 | 0.6% | 1% | 1.5% |
| 5 | 1.2% | 1.5% | 2.5% |
| 10 | 2.0% | 3.2% | 4.2% |
| 20 | 4.0% | 5.5% | 8.0% |
| 30 | 6.2% | 8.0% | 10% |

As is clear from the results, the moisture permeability of films made from the dispersions remains quite low even where a longer period of observation is applied. Due to the method of manufacturing, the films exhibited a porous structure which leaves room for the conclusion that, should the porosity be eliminated, lower values are obtainable.

EXAMPLE 11

The Effect of the Amount of Polyvinyl Alcohol on the Particle Size of the Dispersion In the formulation of the dispersion of Example 10, the amount of polyvinyl alcohol was altered by 3.7% w/w and by 4.9% w/w, and the particle size of the dispersions was observed using a light mnicroscope and a particle size analyzer (Nicomp®) based on light scattering. With the smallest amount of polyvinyl alcohol, the largest particles had a size of 25 to 40 $\mu$m and the smallest of 7 to 13 $\mu$m based on light microscope measurements. The particle size of this dispersion was so great that it was beyond the measurement range of the Nicomp apparatus. As the amount of polyvinyl alcohol was increased to 4.3%, the size of the largest particles was in the order of 20 $\mu$m, that of the medium-sized 10 $\mu$m, and that of the small particles 1.5 to 3.4 $\mu$m based on a Nicomp measurement. When the amount of polyvinyl alcohol was further increased, the size of the largest particles had been reduced to 13 to 16 $\mu$m and that of the medium-sized to 7 $\mu$m. However, the majority of the particles were srnall. By a measurement based on light scattering, sizes of 0.3 to 0.6 $\mu$m and 2.9 to 6.5 $\mu$m were obtained for these particles.

To sum up, the results show that an increase in the amount of polyvinyl alcohol will reduce the particle size of the dispersion.

EXAMPLE 12

The Influence of Different Plasticizers on the Particle Size of the Dispersion The formulation of the dispersion of example 11 was altered such that half the amount of triacetin was replaced by triethyl citrate. The particle size of the dispersions was measured as described in Example 11.

In the dispersion containing triethyl citrate the size of the largest particles, studied by means of a light microscope, was reduced by half, and Nicomp measurements provided the following sizes for the small particles: 0.1 to 0.2 $\mu$m (97.5%) and 1.1 to 2.5 $\mu$m (2.5%).

The particle size of a dispersion where all of the triacetin is replaced by triethyl citrate is of the same order as that of a mixture where both plasticizers are present in equal amounts.

EXAMPLE 13

Storage Stability of Dispersions

Disiersion formulations according to the following table were prepared. The proportions of elements are displayed in percentages by weight.

TABLE 4

Storage stability of dispersions

| Raw materials | Composition 1 | Composition 2 | Composition 3 |
| --- | --- | --- | --- |
| Starch acetate DS 2.8 a) | 13.1% | 14.2% | 13.6% |
| Triacetin | 22.9% | — | 11.9% |
| Triethyl citrate | — | 16.0% | 8.5% |
| Polyvinyl alcohol | 4.2% | 5.0% | 4.4% |
| Water | 58.8% | 64.1% | 61.0% |
| Foam inhibitor b) | 1.0% | 0.7% | 0.6% | a) Starch acetate from enzymatically hydrolyzed barley starch
b) Wacker silicone AS-EM.SLE The dispersions were kept in sealed vessels at room temperature for two months during which time their viscosity stability and changes in particle size during storage were measure, and phase separation, if any, was controlled.

The dispersion viscosities were measured with a Haake Viscotester VT-02 (Ser.no. 3722) as a function of time. The following table lists the measured viscosities:

TABLE 5

Viscosities of dispersions

| | Viscosities, Poise | | | | |
| --- | --- | --- | --- | --- | --- |
| Dispersion | 0 days | 10 days | 20 days | 30 days | 40 days |
| Composition 1 | 15 | 15 | 14 | 12.5 | 12 |
| Composition 2 | 20 | 19 | 18 | 18 | 19 |
| Composition 3 | 18 | 18 | 18 | 18 | 18.5 |

The viscosities of the dispersions underwent no essential changes during storage, which indicates a good level of stability.

The particle sizes of the triacetin-based dispersion (Composition 1) were measured immediately after production and 1 and 2 months after production. The measurements were performed both with a light microscope and with techniques based on light scattering (Nicomp). In Nicomp measurements, the small particles exhibited no alterations of size during the two months. The light microscope revealed a small increase in the size of the large particles during storage.

No visual observation of phase separation in the dispersions during storage could be made.

EXAMPLE 14

The Preparation of a Starch Acetatc Succinate Based Dispersion

The preparation was carried out in the manner described for starch acetate dispersions. The composition of the formulation was as follows: 13.7% w/w of starch acetate succinate ($DS_{ACI}$ 1.34 and $DS_{Sue}$ 0.25),23.9% triacetin, 4.4% of polyvinyl alcohol and 58.0% of water. The starch acetate succinate had been prepared in the manner described in U.S. Pat. No. 08/498341. No phase separation took place in the dispersion during storage.

EXAMPLE 15

Use of Dispersions in Labelling Adhesives

Adhesive formulations were made from the dispersions using tall oil resin-based tackifying resin dispersions as tackifying resin components. The dispersion was applied to a glass plate by means of an application stick. The adhesive was relocated from the glass plate to a strip of labelling paper (50×120 mm) by rolling whereafter the labelling strip was adhered to another glass plate by rolling such that no air bubbles remand in the adhesive surface. The label was adhered to the glass plate such that the adhering surface was 5×100 mm. The adhered labels were air treated for 24 hours (34° C., RH 50%). The time required for removing by washing was determined for the adhesives by placing a 20 g weight on the part of the label outside the adhesive surface and by then placing the glass plate with weight in a basin containing cold water, whereby the cold water circulation of the basin was on all the time. Timing started when the plate plunged and the time lapsed before the label was detached was measured. The test indicates the adhesiveness of botne labels under moist conditions.

TABLE 6

Removability by washing of labelling adhesives

| Test | Dispersion Example | Tackifying resin Oulutac 30D | Tackifying resin Snowtack 301A | Tackifying resin Snowtack 377F | Time required for removal by washing |
|---|---|---|---|---|---|
| 1 | 150 g | 150 g | | | >10 h |
| 2 | 150 g | 32 g | | | 2 h 30 min |
| 3 | 150 g | 18 g | | | 42 min |
| 4 | 150 g | | 21.5 g | | 2 h 5 min |
| 5 | 150 g | | | 21.5 g | 1 h 50 min |
| Dispersion Example 1 | | | | | 50 min |
| Commercially available labelling adhesive | | | | | 2 h 10 min |

Oulutac 30D; Manufacturer Forchem Oy
Snowtack 301A and 377F, Manufacturer Akzo Nobel

EXAMPLE 16

Use of Dispersion as Primer Agent in Extrusion Coating

The dispersion of Example 2 was used for the extrusion coating of paper and board by first manufacturing board coated with the dispersion using a manual application device. Then the dispersion-coated board (the so called lower web) was subjected to application of film by means of a Brabender Plasti-Corder film extruder (having a geometry of 20*0.8*100, lip distance 0.5 mm), which film was cooled between a press roll or nip roll and a cooling roll while the film adhered to the surface of the dispersion-coated board.

The purpose of primer aeents is to enhance the adherence of extrusion coating materials to board or paper, that is, the adhesion between the coating and the board.

The adhesion between the coating and the board was determined by a so called T-peel-test according to the standard ASTM D1876-72. According to the method the material testing apparatus determined the force needed to detach the coating from the board surface.

The primer quality of the dispersion was tested by comparing the adhesion of the materials described by P. Salmi in his engineering thesis [1] to a primed and an unprimed lower web.

| Material | T-peel value [N/m] | |
|---|---|---|
| | Unprimed board | Dispersion-primed board |
| C6L50-CT | 9-26 | p( > 120) | p=the board was peeled whereby, when the coating was pulled at, the board was torn remaining adhered to the coating. A complete adhesion was attained.

[1] Salmi p., Tärkkelysbiopolymeeri eksauusiopä allystyksessä, Engineering Thesis, 1995. Tampere University of Technology, Tampere, 156 p. [Starch-based biopolymer in extrusion coating.]

EXAMPLE 17

Biodegradability of the Starch Acetate Dispersion

The biodegradability of the dispersion prepared according to Example 2 was tested by a test based on an assay of the carbon dioxide formed during biodegradation, whereby a sample was incubated in an inoculant from purified waste water from an activated sludge plant at +25 to 30° C. The formed carbon dioxide is absorbed into a KOH solution, whereby potassium carbonate is formed which is then further analyzed for carbon dioxide. When calculating biodegradability according to the following forrmula: Biodegradability (%)=(measured $CO_2$/theoretically released $CO_2$) *100, the result is obtained that 65% of the sample is degraded within as little as 6 d, and after 13 d, 73% is degraded. The general rule is that a sample is biodegradable if the tested production of carbon dioxide achieves 60 to 70% of the theoretical level.

EXAMPLE 18

Degradation of Dispersion-Coated Board in a Compost

The degradability of board coated with the dispersion prepared in Example 2 was tested in a compost environment with real composting conditions. natural aeration and monitoring of activity parameters (temperature, humidity, $CO_2$, $O_2$, C/N ratio). The test was run at VTT (Technical Research Centre of Finland), Biotechnology and Food Research. The test apparatus consisted of composters coupled to automatic measuring equipmpent for CO, and temperature. The composts were filled and attended to according to a carefully devised plan. The degradation of the test samples was observed visually each week when the biowaste was turned over. Based on such visual observation, the sample was degraded to a degree of about 80% within 70 days, according to the decrease in weight a 90% degradation was attained.

EXAMPLE 19

Coating of Pharmaceutical Tablets

Pharmaceutical Tablets consisting of propanolol hydrochloride (25% w/w) as active substance, dicalcium phosphate dihydrate (74% w/w) as filler/binder, and magnesium stearate (1% w/w) as lubricanL were compressed using a Fette Perfecta 1 rotary tablening machine. The concave tablets had a diameter of 7 mm and they weighed about 120 mg. The tablets were coated with the water dispersion of starch described in Example 2. The tablets were immersed in the dispersion which had been diluted by adding 30% (w/w) of purified water. After immersion, the coating layer formed on the tablets was dried using pressurized air. Air pressure and temperature (25° C.) as well as the position of the tablet in the air current were kept constant. Immersion was repeated two or four times. The coating created on the tablet was even and intact. After two immersions, the coating laver formed was 0.043 mm thick, and after four immersions, its thickness was 0.280 mnm.

The release of active substance (i.e. propanolol hydrochloride) from the tablets was tested using the rotating basket dissolution method described in the US pharmacopoeia (USP XXIII). The tablet was placed in a wire basket which was immersed in a 40 mM phosphate buffer solution whose temperature was 37° C. and whose pH was 7.0 and volume 900 ml. The basket was roteted at a rotation velocity of 100 rpm. At selected points of time, 1.0 ml samples were withdrawn from the buffer solution and subjected to spectrophotornetric drug content measurement at a wavelength of 289 nm.

The release of active substance was measured in three parallel tests from tablets coated in two different ways and from uncoated tablets.

The release of active subiance from the tablets is shown in Table 7 and as a function of time in the annexed FIGURE.

TABLE 7

Release of active substance from coated tablets

Amount of released active substance. %

| Time min | Uncoated tablet | Coating thickness 0.043 mm | Coating thickness 0.280 mm |
|---|---|---|---|
| 1 | 9.75 | 0 | 0 |
| 5 | 19.83 | 0.08 | 0 |
| 10 | 28.86 | 0.29 | 0 |
| 30 | 47.44 | 6.0 | 0 |
| 60 | 64.17 | 14.65 | 0 |
| 120 | 79.23 | 26.84 | 1.18 |
| 180 | 81.01 | 36.57 | 5.54 |
| 240 | 81.50 | 41.78 | 9.73 |
| 300 | 84.92 | 47.07 | 12.64 |
| 360 | 83.07 | 51.03 | 19.07 |
| 480 | 82.32 | 56.17 | 21.38 |
| 720 | 85.38 | 61.96 | 34.20 |
| 1500 | 86.12 | 73.12 | 47.30 |

As is clear from the above Table and the annexed FIGURE, active substance was fully released from uncoated tablets within 2 to 3 hours. Coating the tablets with an aqueous dispersion of starch acetate clearly retarded the release of the active substance. The thicker the coating layer covering the tablet, the slower the release of the active substance.

Based on the present example, an aqueous dispersion of starch acetate is suited for coating pharmaceutical tablets. The rate of release of the medicinal substance from the tablets can be controlled bv controlling the thickness of the starch acetate film formned. Mdification of the aqueous dispersion formulation of the starch acetate, for instance by changing particle size, plasticizer, or protective colloid, provides further possibilities of optimizing the release profile of the active substance.

What is claimed is:

1. A hydrophobic polymer dispersion containing modified starch dispersed in a liquid phase together with dispersion admixtures known as such, characterized in that the modified starch comprises (i) a starch ester prepared from native starch and having a degree of substitution (DS) greater than 1.5, wherein the starch ester is an ester formed by starch and one or more aliphatic carboxylic acids containing 2 to 24 carbon atoms and (ii) 1 to 95% by weight of a plasticizer.

2. The polymer dispersion of claim 1, wherein the carboxylic acid component of the ester is derived from acetic acid, propionic acid or butyric acid, or a mixture thereof.

3. The polymer dispersion of claim 1, wherein the carboxylic acid component is derived from a saturated or an unsaturated native fatty acid.

4. The polymer dispersion of claim 3, wherein the carboxylic acid component is derived from palmitic acid, stearic acid, oleic acid, linoleic acid, or a mixture thereof.

5. The polymer dispersion of claim 1, wherein the starch ester is a mixed ester of starch and acetic acid and stearic acid.

6. The polymer dispersion of claim 1, wherein the degree of substitution (DS) of the starch ester is in the range from 2.0 to 3.0.

7. The polymer dispersion of claim 1, wherein the starch raw material is selected from the group consisting of native starch, oxidized starch, hydrolyzed starch, crosslinked starch and cationic starch, the starch having an amylose content of 0 to 100% and an amylopectin content of 100 to 0%.

8. The polymer dispersion of claim 7, wherein the dispersion contains polyvinyl alcohol, cationic starch and/or hydroxyalkyl starch as a dispersion admixture.

9. The polymer dispersion of claim 1, wherein the dispersion contains alkyl-ketene dimer (AKD) wax or beeswax as a dispersion admixture.

10. A hydrophobic polymer dispersion according to claim 1 containing modified starch dispersed in a liquid phase together with dispersion admixtures known as such, wherein the modified starch comprises 1 to 50% by weight of a plasticizer.

11. The polymer dispersion of claim 1, comprising
5 to 25 parts by weight of a starch ester,
5 to 50 parts by weight of a plasticizer,
1 to 150 parts by weight of water, and
1 to 20 parts by weight of a dispersion admixture.

12. The polymer dispersion of claim 1, wherein it further contains 0.01 to 30% by weight, of a cellulose ester such as cellulose acetate, propionate or buryrate, or a mixed ester thereof.

13. A process for the formation of a hydrophobic polymer dispersion containing modified starch dispersed in a liquid phase together with dispersion admixtures known as such, characterized in that the modificd starch comprises (i) a starch ester prepared from native starch and having a degree of substitution (DS) greater than 1.5, wherein the starch ester is an ester formed by starch and one or more aliphatic carboxylic acids containing 2 to 24 carbon atoms and (ii) 1 to 95% by weight of a plasticizer, wherein said process includes the steps:
the polymer is dispersed in water
using a biodegradable polymer as polymer,
first mixing the polymer with a plasticizer in order to obtain a plasticized polymer blend,
mixing the plasticized polymer blend, with dispersion admixtures and water in order to obtain a dispersion, the mixing being carried out at an elevated temperature.

14. The process of claim 13, wherein the polymer is mixed with the plasticizer at an elevated temperature.

15. The process of claim 13, wherein the polymer is mixed with the plasticizer in a melt processing machine.

16. The process of claim 13, wherein the polymer used is selected from the group consisting of a starch ester derived from native starch, hydrolyzed starch, oxidized starch, crosslinked starch or gelatinized starch, a starch ether, a mixed ester/ether of starch, grafted starch and/or polycaprolactone, lactic acid polymers, polylactide and polyhydroxybutyrate/-valerate.

17. The process of claim 13, wherein the plasticizer used is selected from the group consisting of triacetin, diacetin, monoacetin, triethyl citrate, tributyl citrate, acetyl triethyl citrate, acetyl tributyl citrate, dimethyl succinate, diethyl succinate, ethyl lactate, methyl lactate, a fatty acid ester of glycerol, castor oil, olive oil, rapeseed oil, tall oil, dibutyl phthalate, diethyl phthalate, and mixtures thereof.

18. The process of claim 13, wherein polyvinyl alcohol, cationic starch and/or hydroxyalkyl starch is used as admixture.

19. The process of claim 18, wherein the weight-average molar mass of the polyvinyl alcohol is about 10,000 to 115,000.

20. The process of claim 13, wherein alkyl-ketene dimer (AKD) wax or beeswax is used as the dispersion admixture.

21. The process of claim 13, wherein 5 to 25 parts by weight of starch ester are mixed with 5 to 50 parts by weight of plasticizer in order to obtain a plasticized starch ester mixture, during the mixing, the liquid phase is kept at a temperature of about 100 to 180° C., and 1 to 150 parts by weight of water and 1 to 20 parts by weight of a dispersion admixture are added to the plasticized starch ester mixture, whereby the liquid phase is kept at a ternperature of about 50 to 100° C. while adding the water.

22. The process of claim 21, wherein, first, the admixture and then the water are added to the plasticized starch.

23. The process of claim 21, wherein the admixture is first dissolved in water which is then added to the plasticized starch.

24. The process of claim 21, wherein the water and the admixture are gradually added to the plasticized starch.

25. The process of claim 24, wherein the water and the admixture are added with a rate allowing the plasticized mass to remain homogeneous without any separation of phases.

26. The process of claim 13, wherein 5 to 25 parts by weight of a starch ester.

5 to 50 parts by weight of a plasticizer and 1 to 20 parts by weight of an admixture are intermixed in a polymer melt processing machine at a temperature of 100 to 250° C. in order to form a plasticized starch ester blend, and the plasticized starch ester blend is admixed with 1 to 150 parts by weight of water at a temperature of about 50 to 100° C. in order to forrn a hydrophobic dispersion.

27. A method of coating a substrate which comprises applying to the substrate a coating which comprises a hydrophobic polymer dispersion containing modified starch dispersed in a liquid phase together with dispersion admixtures known as such, characterized in that the modified starch comprises (i) a starch ester prepared from nativc starchand having a degree of substitution (DS) greater than 1.5, wherein the starch ester is an ester formed by starch and one or more aliphatic carboxylic acids containing 1 to 24 carbon atoms and (ii) 1 to 15% by weight of a plasticizer.

28. The method according to claim 27, wherein the substrate is selected from the group consisting of paper, board and medicinal tablets.

29. A method of manufacturing a primer composition for paint which comprises formulating said primer composition with a hydrophobic polymer dispersion containing a modified starch ester dispersed in a liquid phase wherein the modified starch comprises (i) a starch ester prepared from native starch and having a degree of substitution (DS) greater than 1.5, wherein the starch ester is an ester formed by starch and one or more aliphatic carboxylic acids containing 1 to 24 carbon atoms and (ii) 1 to 15% by weight of a plasticizer.

30. A method of manufacturing a labeling adhesive composition which comprises formulating said adhesive composition with a hydrophobic polymer dispersion containing modified starch dispersed in a liquid phase together with dispersion admixtures known as such, characterized in that the modified starch comprises (i) a starch ester prepared from native starch and having a degree of substitution (DS) greater than 1.5, wherein the starch ester is derived from an ester formed by starch and one or more aliphatic carboxylic acids containing 2 to 24 carbon atoms and (ii) 1 to 95% by weight of a plasticizer.

31. A method of manufacturing a cast film composition which comprises formulating said cast film composition with a hydrophobic polymer dispersion containing modified starch dispersed in a liquid phase together with dispersion admixtures known as such, characterized in that the modified starch comprises (i) a starch ester prepared from native starch and having a degree of substitution (DS) greater than 1.5, wherein the starch ester is derived from an ester formed by starch and one or more aliphatic carboxylic acids containing 2 to 24 carbon atoms and (ii) 1 to 95% by weight of a plasticizer.

32. A method of manufacturing a binding agent composition for materials containing cellulose fibers which comprises formulating said binding agent composition with a hydrophobic polymer dispersion containing modified starch dispersed in a liquid phase together with dispersion admixtures known as such, characterized in that the modified starch comprises (i) a starch ester prepared from native starch and having a degree of substitution (DS) greatcr than 1.5, wherein the starch ester is derived from an ester formed by starch and one or more aliphatic carboxylic acids containing 2 to 24 carbon atoms and (ii) 1 to 95% by weight of a plasticizer.

33. The polymer dispersion of claim 2, wherein the starch ester contains a mixture of both short chain carboxylic acid components having two to four carbon atoms per molecule and long chain carboxylic acid components having greater than 4 carbon atoms per molecule.

34. The polymer dispersion of claim 1, wherein the dispersion contains a plasticizer selected from the group consisting of triacetin, diacetin, monoacetin, triethyl citrate, tributyl citrate, acetyl tricthyl citrate, acetyl tributyl citrate, dimethyl succinate, diethyl succinate, ethyl lactate, methyl lactate, a fatty acid ester of glycerol, castor oil, olive oil, rapeseed oil, tall oil, dibutyl phthalatc, diethyl phthalate, and mixtures thereof.

35. The process according to claim 13, wherein the admixtures and water are homogenized.

\* \* \* \* \*